(12) United States Patent
Tietze et al.

(10) Patent No.: US 6,521,780 B1
(45) Date of Patent: Feb. 18, 2003

(54) CYCLOALKYL DERIVATIVES AND THE SOLID-PHASE SYNTHESIS OF SUCH DERIVATIVES

(75) Inventors: Lutz F. Tietze, Göttingen (DE); Adrian Steinmetz, Göttingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/142,775

(22) PCT Filed: Mar. 6, 1997

(86) PCT No.: PCT/EP97/01127

§ 371 (c)(1),
(2), (4) Date: Sep. 14, 1998

(87) PCT Pub. No.: WO97/34852

PCT Pub. Date: Sep. 25, 1997

(30) Foreign Application Priority Data

Mar. 15, 1996 (DE) .......................................... 196 10 103

(51) Int. Cl.⁷ .......................... C07C 69/74; C07C 59/00
(52) U.S. Cl. ........................ 560/127; 560/128; 560/129; 560/170; 562/579; 564/1; 568/700; 436/518; 436/536
(58) Field of Search .................................. 436/536, 518, 436/7.1; 560/127, 128, 129, 170; 562/579; 564/1; 568/700

(56) References Cited

U.S. PATENT DOCUMENTS 5,288,514 A   2/1994 Ellman
5,565,324 A * 10/1996 Still et al. ...................... 435/6

FOREIGN PATENT DOCUMENTS

| WO | 92/00091 | 1/1992 |
| WO | 95/16712 | 6/1995 |
| WO | 95/30642 | 11/1995 |
| WO | 96/00148 | 1/1996 |
| WO | 96/00391 | 1/1996 |

OTHER PUBLICATIONS

Jr. of the Gesellschaft, 24/12 1985, 1042–1043.
Jr. of the Gesellschaft, 27/5 1988, 723–758.
Jr. of the Gesellschaft, 27/9 1988, 1201–1226.
Jr. of Org. Chem. vol. 54, No. 13, Jun. 1989,3120–3129.
Jr. of Synt. Org. Chem. 1988, No. 5, May 359–361.
Tetrahedron Ltrs. Tietze et al. vol. 27, No. 16, 1767–1770, 1986.
Int. J. Peptide Protein, Res. 35, 1990, 161–214.
Int. J. Peptide Protein Res. 41, 1993,201–203.
J. Med. Chem., vol. 37, No. 9, Apr. 29, 1994, 1233–1401.
Tetrahedron Ltrs., vol. 34, No. 52, 8549–8552, 1993.
Tetrahedron Ltrs., vol. 31, No. 27, 3857–3858, 1990.

* cited by examiner

Primary Examiner—Bennett Celsa
(74) Attorney, Agent, or Firm—Keil & Weinkauf

(57) ABSTRACT

The invention relates to cycloalkyl derivatives, a process for their preparation and their use.

10 Claims, No Drawings

CYCLOALKYL DERIVATIVES AND THE SOLID-PHASE SYNTHESIS OF SUCH DERIVATIVES

The invention relates to cycloalkyl derivatives, to a process for preparing them and to their use.

TECHNICAL FIELD

In classical research looking for active substances, the biological effect of novel compounds has been tested in random screening on the whole organism, for example the plant or the microorganism. In this case the biological testing was the limiting factor with respect to the synthetic chemistry. The provision of molecular test systems by molecular and cell biology has lead to a drastic change in the situation.

A large number of molecular test systems have been and are being developed for modern research looking for active substances, such as receptor binding assays, enzyme assays and cell-cell interaction assays. Automation and miniaturization of these test systems permits the sample throughput to be high. This development makes it possible to test in ever shorter times a continually increasing number of chemicals for their biological effect in random screening and thus for possible use as lead structure for an active substance in medicine, veterinary medicine or crop protection.

A modern automated test system allows 100,000 or more chemicals to be tested for their biological effect each year in a mass screening.

This development has made classical synthetic chemistry the limiting factor in research looking for active substances.

If the capacity of these test systems is to be fully exploited, there must be a considerable increase in the efficiency of the chemical synthesis of active substance lead structures.

BACKGROUND ART

Combinatorial chemistry can contribute to this necessary increase in efficiency, especially when it makes use of automated solid-phase synthetic methods (see, for example, review on articles J. Med. Chem. 37 (1994) 1233 and 1385). Combinatorial chemistry makes it possible to synthesize a wide variety of different chemical compounds, called substance libraries. Solid-phase synthesis has the advantage that by-products and excess reactants can easily be removed, so that elaborate purification of the products is unnecessary. The finished synthetic products can be passed directly, i.e. carrier-bound, or after elimination from the solid phase, to mass screening. Intermediates can also be tested in the mass screening.

Applications described to date have been mainly confined to the peptide and nucleotide areas (Lebl et al., Int. J. Pept. Prot. Res. 41, 1993: 203 and WO 92/00091) or their derivatives (WO 96/00391). Since peptides and nucleotides have only limited possible uses as drugs because of their unfavorable pharmacological properties, it is desirable to utilize the solid-phase synthetic methods known and established in peptide and nucleotide chemistry for synthetic organic chemistry.

U.S. Pat. No. 5,288,514 reports one of the first combinatorial solid-phase syntheses in organic chemistry outside peptide and nucleotide chemistry. U.S. Pat. No. 5,288,514 describes the sequential solid-phase synthesis of 1,4-benzodiazepines.

WO 95/16712, WO 95/30642 and WO 96/00148 describe other solid-phase syntheses of potential active substances in combinatorial chemistry.

However, in order to be able fully to exploit the possibilities of modern test systems in mass screening, it is necessary continuously to feed novel compounds of maximum structural diversity into the mass screening. This procedure makes it possible considerably to reduce the time for identification and optimization of a novel active substance lead structure.

It is therefore necessary continually to develop novel diverse combinatorial solid-phase syntheses. It is moreover worthwhile to aim at biologically active compounds.

In view of the significance of cycloalkyl derivatives, specifically of cycloalkylmalonic ester derivatives, as potential active substances in the drugs and crop protection sectors, it is of great importance to provide efficient methods for their solid-phase preparation and, in particular, for the subsequent testing in mass screening.

DISCLOSURE OF INVENTION

It is an object of the present invention to provide a rapid and efficient solid-phase process for preparing cycloalkyl derivatives which meets the requirements of combinatorial chemistry.

We have found that this object is achieved by a process for preparing cycloalkyl derivatives of the formula I

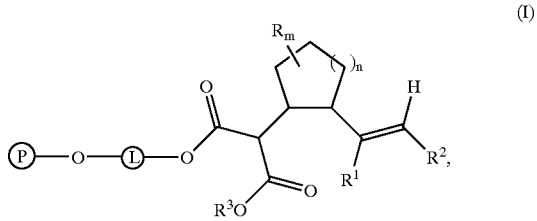

in which the variables and substituents have the following meanings:

(P) a solid phase,
(L) a linker with 2 to 12 carbon atoms or the structure —$CH_2$—$CH_2$—(—O—$CH_2$—$CH_2$—)$_{1-100}$—,
$R^1$ hydrogen or a low molecular weight organic radical,
$R^2$ hydrogen or unsubstituted or substituted alkyl, alkenyl, alkynyl or cycloalkyl or
$R^1$ and $R^2$ together an unsubstituted or substituted 4- to 8-membered ring
$R^3$ unsubstituted or substituted $C_1$–$C_{10}$-alkyl, $C_3$–$C_8$-cycloalkyl or aryl,
R a low molecular weight organic radical or two adjacent R radicals together form an unsubstituted or substituted carbo- or hetero-cyclic ring
n=0 to 4
m=0 to n+2,
which comprises reacting a compound of the formula II

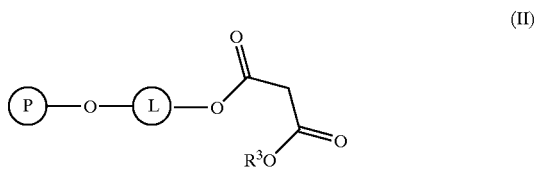

with aldehydes of the formula III

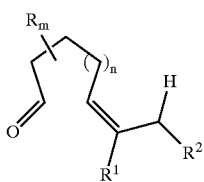

in the presence of a base to give compounds of the formula IV

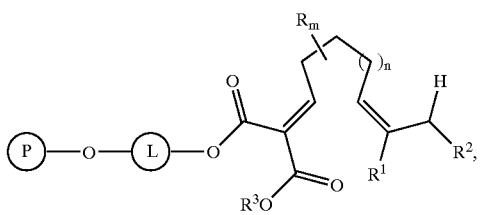

and cyclizing the resulting product IV in the presence of a Lewis acid.

The invention additionally relates to novel cycloalkyl derivatives and to their use.

MODE(S) FOR CARRYING OUT THE INVENTION

It is possible to use as solid phase (P) in the process according to the invention supports known from solid-phase peptide synthesis. Usable supports can, as long as they are compatible with the synthetic chemistry used, consist of a large number of materials. The size of the supports may be varied within wide limits depending on the material. Particles in the range from 1 μm to 1.5 cm are preferably used as supports, and particles in the range from 1 μm to 100 μm are particularly preferred for polymeric supports.

The shape of the supports is immaterial, but spherical particles are preferred. The supports may have a homogeneous or heterogeneous size distribution, but homogeneous particle sizes are preferred.

Examples of suitable solid phases (P) are ceramic, glass, latex, crosslinked polystyrenes, polyacrylamides, silica gels, cellulose particles, resins, gold or colloidal metal particles.

In order to make it possible to attach the reactant and eliminate the product after the synthesis, the support must be suitably functionalized or provided with a linker which has an appropriate functional group. Examples of suitable and preferred supports and support-linker conjugates are chlorobenzyl-resin (Merrifield resin), Rink resin (Novabiochem), Sieber resin (Novabiochem), Wang resin (Bachem), Tentagel resins (Rapp-Polymere), Pega resin (Polymer Laboratories) or polyacrylamides. Particularly preferred supports are chlorobenzyl-resins, Tentagel resins or polyacrylamides. For attachment of the preferred linker

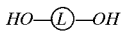

with 2 to 12 carbon atoms to the solid phase, the latter must where appropriate be modified in a manner to the skilled worker. The linker can be branched or unbranched, chiral or achiral.

Examples of diols which may be mentioned are ethylene glycol, 1,3-propanediol, 1,2-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,4-pentanediol, 2-methyl-1,4-butanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 2-methyl-1,5-pentanediol or 3-methyl-1,5-pentanediol.

To determine the concentration of hydroxyl groups on the linker-coupled resin, the latter was reacted with 3,5-dinitrobenzoyl chloride in pyridine, and nitrogen determination on the resulting ester is a measure of the hydroxyl group concentration. This is in the range from 0.5 to 0.85 mmol of hydroxyl groups per gram of resin.

Polyacrylamides [(P)—$NH_2$] can be derivatized, for example, with 4-chloromethylbenzoic acid in such a way that the doubly deprotonated linker can be attached (Scheme I).

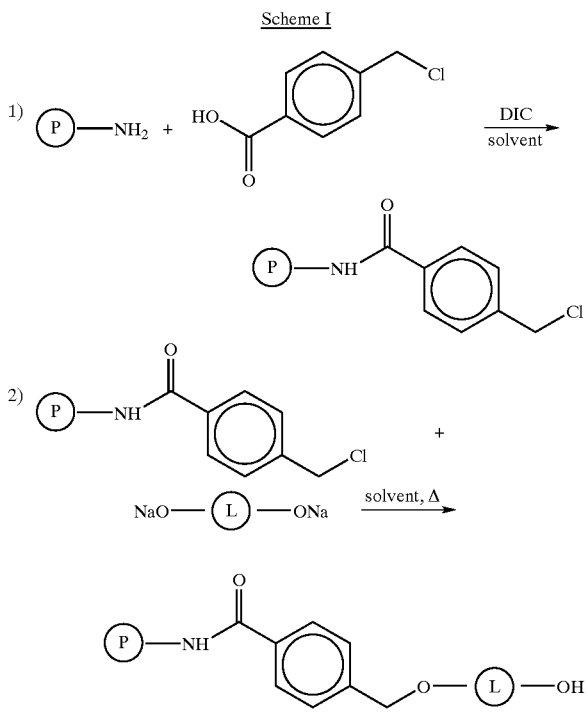

Scheme I

The amide linkage (1) between the support and the 4-chloromethylbenzoic acid can be formed in the solvent with the aid of, for example, diisopropylcarbodiimide (=DIC). Other coupling reagents suitable for forming the amide linkage are, for example, TBTU, HBTU, BOP or PYBOP (Lit.: Int. J. Peptide Prot. Rev. 35, 1990: 161–214).

Suitable solvents for forming the functionalized solid phase are aprotic, nonpolar or polar solvents, for example DMF, $CH_2Cl_2$, DMSO or THF. It is possible to use single solvents or mixtures.

The coupling of the preferred linker to the Merifield [sic] resin can take place directly in the doubly deprotonated form of the linker (Scheme I,2) in the presence of the solvents described above.

Reaction (2) is carried out at from 30 to 150° C., preferably from 60 to 100° C.

The product I can be eliminated from the solid phase by reduction, transesterification, amidation or base catalysis.

$R^1$ in the compounds of the formulae I, III, IV and VI is hydrogen or a low molecular weight organic radical which may contain 1 to 26 carbon atoms in addition to, where appropriate, at least one oxygen and/or at least one hetero atom.

Low molecular weight organic radicals which may be mentioned for $R^1$ are unsubstituted or substituded alkyl, alkenyl, alkynyl, cycloalkyl, cycloalkenyl, cycloalkynyl, aryl, hetaryl, alkylaryl, alkylhetaryl, alkylcarbonyl, arylcarbonyl, alkylsulfonyl or arylsulfonyl radicals.

Alkyl radicals which may be mentioned are branched or unbranched $C_1$–$C_8$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl.

Suitable substituents are one or more substituents such as halogen, such as fluorine, chlorine or bromine, cyano, nitro, amino, hydroxyl, thio, alkyl, aryl, alkoxy, carboxyl, benzyloxy, phenyl or benzyl.

Alkenyl radicals which may be mentioned are branched or unbranched $C_1$–$C_8$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl.

Suitable substituents are one or more substituents such as halogen, such as fluorine, chlorine or bromine, cyano, nitro, amino, hydroxyl, thio, alkyl, aryl, alkoxy, carboxyl, benzyloxy, phenyl or benzyl.

Alkynyl means $C_2$–$C_6$-alkynyl radicals such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yl-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl.

The alkynyl radical may be unsubstituted or substituted by one or more substituents such as halogen, such as fluorine, chlorine or bromine, cyano, nitro, amino, hydroxyl, thio, alkyl, aryl, alkoxy, carboxyl, benzyloxy, phenyl or benzyl.

Cycloalkyl radicals which may be mentioned are $C_3$–$C_8$-cycloalkyl chains such as cyclopropyl, cyclobutyl, cyclopentyl, cyclohexyl, cycloheptyl or cyclooctyl.

Suitable substituents are one or more radicals such as halogen, such as fluorine, chlorine or bromine, cyano, nitro, amino, hydroxyl, thio, alkyl, aryl, alkoxy, carboxyl, benzyloxy, phenyl or benzyl.

Aryl radicals mean simple or fused aromatic ring systems which may be unsubstituted or substituted by one or more radicals such as halogen, such as fluorine, chlorine or bromine, cyano, nitro, amino, hydroxyl, thio, alkyl, alkoxy or other radicals.

Preferred aryl radicals are phenyl or naphthyl.

Hetaryl radicals mean simple or fused aromatic ring systems with one or more heteroaromatic 3- to 7-membered rings, which may be unsubstituted or substituted by one or more radicals such as halogen, such as fluorine, chlorine or bromine, cyano, nitro, amino, hydroxyl, thio, alkyl, alkoxy or other radicals.

The ring or ring system may contain one or more nitrogen, sulfur and/or oxygen atoms as hetero atoms.

Alkylaryl radicals which may be mentioned are $C_1$–$C_6$-alkylphenyl or $C_1$–$C_6$-alkylnaphthyl radicals which have branched or unbranched chains, such as methylphenyl, ethylphenyl, propylphenyl, 1-methylethylphenyl, butylphenyl, 1-methylpropylphenyl, 2-methylpropylphenyl, 1,1-dimethylethylphenyl, pentylphenyl, 1-methylbutylphenyl, 2-methylbutylphenyl, 3-methylbutylphenyl, 2,2-dimethylpropylphenyl, 1-ethylpropylphenyl, n-hexylphenyl, 1,1-dimethylpropylphenyl, 1,2-dimethylpropylphenyl, 1-methylpentylphenyl, 2-methylpentylphenyl, 3-methylpentylphenyl, 4-methylpentylphenyl, 1,1-dimethylbutylphenyl, 1,2-dimethylbutylphenyl, 1,3-dimethylbutylphenyl, 2,2-dimethylbutylphenyl, 2,3-dimethylbutylphenyl, 3,3-dimethylbutylphenyl, 1-ethylbutylphenyl, 2-ethylbutylphenyl, 1,1,2-trimethylpropylphenyl, 1,2,2-trimethylpropylphenyl, 1-ethyl-1-methylpropylphenyl, 1-ethyl-2-methylpropylphenyl, methylnaphthyl, ethylnaphthyl, propylnaphthyl, 1-methylethylnaphthyl, butylnaphthyl, 1-methylpropylnaphthyl, 2-methylpropylnaphthyl, 1,1-dimethylethylnaphthyl, pentylnaphthyl, 1-methylbutylnaphthyl, 2-methylbutylnaphthyl, 3-methylbutylnaphthyl, 2,2-dimethylpropylnaphthyl, 1-ethylpropylnaphthyl, n-hexylnaphthyl, 1,1-dimethylpropylnaphthyl, 1,2-dimethylpropylnaphthyl, 1-methylpentylnaphthyl, 2-methylpentylnaphthyl, 3-methylpentylnaphthyl, 4-methylpentylnaphthyl, 1,1-dimethylbutylnaphthyl, 1,2-dimethylbutylnaphthyl, 1,3-dimethylbutylnaphthyl, 2,2-dimethylbutylnaphthyl, 2,3-dimethylbutylnaphthyl, 3,3-dimethylbutylnaphthyl, 1-ethylbutylnaphthyl, 2-ethylbutylnaphthyl, 1,1,2-trimethylpropylnaphthyl, 1,2,2-trimethylpropylnaphthyl, 1-ethyl-1-methylpropylnaphthyl, 1-ethyl-2-methylpropylnaphthyl.

The alkylaryl radicals may be unsubstituted or substituted by one or more radicals such as halogen, such as fluorine, chlorine or bromine, cyano, nitro, amino, hydroxyl, thio, alkyl, alkoxy or other radicals.

Alkylhetaryl means $C_1$–$C_8$-alkylhetaryl radicals which have branched or unbranched chains and contain one or more nitrogen, sulfur and/or oxygen atoms in the ring or ring system.

The alkylheteryl radicals may be unsubstituted or substituted by one or more radicals such as halogen, such as fluorine, chlorine or bromine, cyano, nitro, amino, hydroxyl, thio, alkyl, alkoxy or other radicals.

Alkylcarbonyl radicals which may be mentioned are branched or unbranched $C_1$–$C_4$-alkylcarbonyl chains such as acetyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl.

A suitable arylcarbonyl radical is benzoyl or naphthoyl.

Alkylsulfonyl is, for example, methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl.

Arylsulfonyl radicals which may be mentioned are phenylsulfonyl or naphthylsulfonyl.

All alkylcarbonyl, arylcarbonyl, alkylsulfonyl and arylsulfonyl radicals may be unsubstituted or substituted by one or more radicals such as halogen, such as fluorine, chlorine or bromine, cyano, nitro, amino, hydroxyl, thio, alkyl, alkoxy or other radicals.

Radicals which may be mentioned for $R^2$ in the compounds of the formulae I, III, IV or VI are hydrogen or unsubstituted or substituted alkyl, alkenyl, alkynyl or cycloalkyl, where alkyl means branched or unbranched $C_1$–$C_8$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl;

alkenyl means branched or unbranched $C_1$–$C_8$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl.

alkynyl means branched or unbranched $C_2$–$C_6$-alkynyl chains such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yl-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and cycloalkyl means $C_3$–$C_8$-cycloalkyl chains such as cyclopropyl, cyclobutyl, cyclopentyl, cyclohexyl, cycloheptyl or cyclooctyl.

$R^1$ and $R^2$ may together form an unsubstituted or substituted 4- to 8-membered ring.

All the $R^2$ radicals mentioned may be unsubstituted or substituted by at least one other radical from the group of halogen, such as fluorine, chlorine or bromine, cyano, nitro, amino, hydroxyl, thio or other radicals.

Radicals which may be mentioned for $R^3$ in the compounds of the formulae I, II, IV, VI and VII are unsubstituted or substituted $C_1$–$C_{10}$-alkyl, $C_3$–$C_8$-cycloalkyl or aryl, where alkyl means branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl, where the alkyl radical may be substituted by an unsubstituted or substituted aromatic or heteroaromatic ring;

cycloalkyl means, for example, cyclopropyl, cyclobutyl, cyclopentyl, cyclohexyl, cycloheptyl or cyclooctyl.

aryl means phenyl or naphthyl.

All the radicals mentioned may be unsubstituted or substituted by at least one other radical from the group of halogen, such as fluorine, chlorine or bromine, cyano, nitro, amino, hydroxyl, thio or other radicals.

R in the compounds of the formulae I, III, IV and VI is a low molecular weight organic radical which may contain 1 to 26 carbon atoms in addition to, where appropriate, at least one oxygen and/or at least one hetero atom.

Low molecular weight organic radicals which may be mentioned for R are unsubstituted or substituted alkyl, alkenyl, alkynyl, cycloalkyl, aryl, hetaryl, alkylaryl, alkylhetaryl, alkylcarbonyl, arylcarbonyl, alkylsulfonyl or arylsulfonyl.

Alkyl radicals which may be mentioned are branched or unbranched $C_1$–$C_8$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl.

Suitable substituents are one or more substituents such as halogen, such as fluorine, chlorine or bromine, cyano, nitro, amino, hydroxyl, thio, alkyl, aryl, alkoxy, carboxyl, benzyloxy, phenyl or benzyl.

Alkenyl radicals which may be mentioned are branched or unbranched $C_1$–$C_8$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl.

Suitable substituents are one or more substituents such as halogen, such as fluorine, chlorine or bromine, cyano, nitro, amino, hydroxyl, thio, alkyl, aryl, alkoxy, carboxyl, benzyloxy, phenyl or benzyl.

Alkynyl means $C_2$–$C_6$-alkynyl radicals such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yl-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl.

The alkynyl radical may be unsubstituted or substituted by one or more substituents such as halogen, such as fluorine, chlorine or bromine, cyano, nitro, amino, hydroxyl, thio, alkyl, aryl, alkoxy, carboxyl, benzyloxy, phenyl or benzyl.

Cycloalkyl radicals which may be mentioned are $C_3$–$C_8$-cycloalkyl chains such as cyclopropyl, cyclobutyl, cyclopentyl, cyclohexyl, cycloheptyl or cyclooctyl.

Suitable substituents are one or more radicals such as halogen, such as fluorine, chlorine or bromine, cyano, nitro, amino, hydroxyl, thio, alkyl, aryl, alkoxy, carboxyl, benzyloxy, phenyl or benzyl.

Aryl radicals mean simple or fused aromatic ring systems which may be unsubstituted or substituted by one or more radicals such as halogen, such as fluorine, chlorine or bromine, cyano, nitro, amino, hydroxyl, thio, alkyl, alkoxy or other radicals.

Preferred aryl radicals are phenyl or naphthyl.

Hetaryl radicals mean simple or fused aromatic ring systems with one or more heteroaromatic 3- to 7-membered rings, which may be unsubstituted or substituted by one or more radicals such as halogen, such as fluorine, chlorine or bromine, cyano, nitro, amino, hydroxyl, thio, alkyl, alkoxy or other radicals.

The ring or ring system may contain one or more nitrogen, sulfur and/or oxygen atoms as hetero atoms.

Alkylaryl radicals which may be mentioned are $C_1$–$C_6$-alkylphenyl or $C_1$–$C_6$-alkylnaphthyl radicals which have branched or unbranched chains, such as methylphenyl, ethylphenyl, propylphenyl, 1-methylethylphenyl, butylphenyl, 1-methylpropylphenyl, 2-methylpropylphenyl, 1,1-dimethylethylphenyl, pentylphenyl, 1-methylbutylphenyl, 2-methylbutylphenyl, 3-methylbutylphenyl, 2,2-dimethylpropylphenyl, 1-ethylpropylphenyl, n-hexylphenyl, 1,1-dimethylpropylphenyl, 1,2-dimethylpropylphenyl, 1-methylpentylphenyl, 2-methylpentylphenyl, 3-methylpentylphenyl, 4-methylpentylphenyl, 1,1-dimethylbutylphenyl, 1,2-dimethylbutylphenyl, 1,3-dimethylbutylphenyl, 2,2-dimethylbutylphenyl, 2,3-dimethylbutylphenyl, 3,3-dimethylbutylphenyl, 1-ethylbutylphenyl, 2-ethylbutylphenyl, 1,1,2-trimethylpropylphenyl, 1,2,2-trimethylpropylphenyl, 1-ethyl-1-methylpropylphenyl, 1-ethyl-2-methylpropylphenyl, methylnaphthyl, ethylnaphthyl, propylnaphthyl, 1-methylethylnaphthyl, butylnaphthyl, 1-methylpropylnaphthyl, 2-methylpropylnaphthyl, 1,1-dimethylethylnaphthyl, pentylnaphthyl, 1-methylbutylnaphthyl, 2-methylbutylnaphthyl, 3-methylbutylnaphthyl, 2,2-dimethylpropylnaphthyl, 1-ethylpropylnaphthyl, n-hexylnaphthyl, 1,1-dimethylpropylnaphthyl, 1,2-dimethylpropylnaphthyl, 1-methylpentylnaphthyl, 2-methylpentylnaphthyl, 3-methylpentylnaphthyl, 4-methylpentylnaphthyl, 1,1-dimethylbutylnaphthyl, 1,2-dimethylbutylnaphthyl, 1,3-dimethylbutylnaphthyl, 2,2-dimethylbutylnaphthyl, 2,3-dimethylbutylnaphthyl, 3,3-dimethylbutylnaphthyl, 1-ethylbutylnaphthyl, 2-ethylbutylnaphthyl, 1,1,2-trimethylpropylnaphthyl, 1,2,2-trimethylpropylnaphthyl, 1-ethyl-1-methylpropylnaphthyl, 1-ethyl-2-methylpropylnaphthyl.

The alkylaryl radicals may be unsubstituted or substituted by one or more radicals such as halogen, such as fluorine, chlorine or bromine, cyano, nitro, amino, hydroxyl, thio, alkyl, alkoxy or other radicals.

Alkylhetaryl means $C_1$–$C_8$-alkylhetaryl radicals which have branched or unbranched chains and which contain one or more nitrogen, sulfur and/or oxygen atoms in the ring or ring system.

The alkylhetaryl radicals may be unsubstituted or substituted by one or more radicals such as halogen, such as fluorine, chlorine or bromine, cyano, nitro, amino, hydroxyl, thio, alkyl, alkoxy or other radicals.

Alkylcarbonyl radicals which may be mentioned are branched or unbranched $C_1$–$C_4$-alkylcarbonyl chains such as acetyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl.

A suitable arylcarbonyl radical is benzoyl or naphthoyl.

Alkylsulfonyl is, for example, methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl.

Arylsulfonyl radicals which may be mentioned are phenylsulfonyl or naphthylsulfonyl.

All alkylcarbonyl, arylcarbonyl, alkylsulfonyl and arylsulfonyl radicals may be unsubstituted or substituted by one or more radicals such as halogen, such as fluorine, chlorine or bromine, cyano, nitro, amino, hydroxyl, thio, alkyl, alkoxy or other radicals.

Two adjacent R radicals may together form an unsubstituted or substituted carbo- or heterocyclic ring. The rings may be saturated, unsaturated with at least one double bond or aromatic. The rings may have 3 to 8 members.

The ring may contain one or more nitrogen, sulfur and/or oxygen atoms as hetero atom.

Examples of substituents which may be mentioned for the rings are halogen, such as fluorine, chlorine or bromine, cyano, nitro, amino, hydroxyl or thio.

The variable n is 0 to 4, preferably 1 or 2.

The variable m in the radical R is 0 to n+2.

The process according to the invention for preparing the cycloalkyl derivatives can be carried out in three separate steps as shown in Scheme II; alternatively, all three steps can be carried out together in a consecutive sequence.

The process according to the invention can be carried out in a series of parallel automated synthesis batches. It is also possible to employ reactant mixtures in one synthesis batch or parallel synthesis batches.

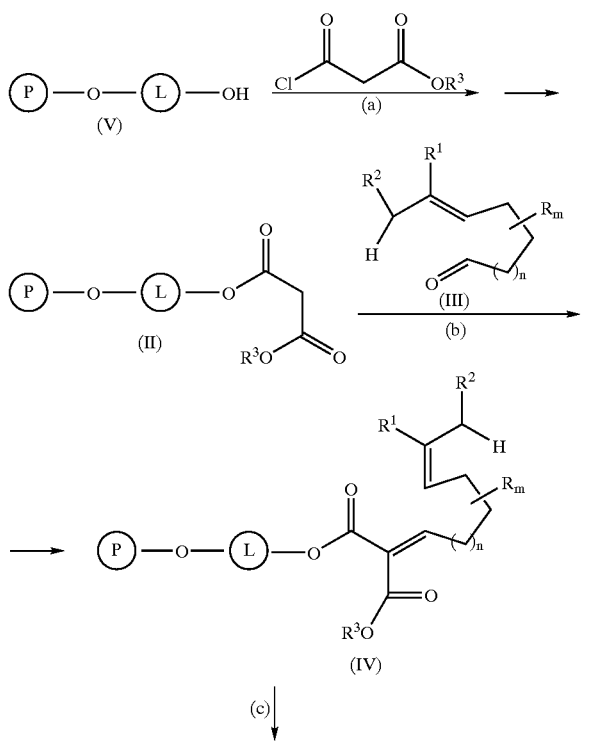

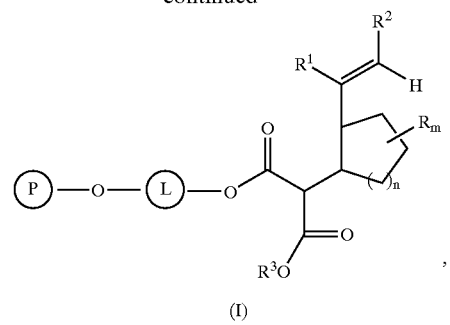

The synthesis can also be stopped at the stage of product IV, and the product can be isolated, directly or-after elimination, and tested in mass screening.

Reaction (a) is carried out in the presence of a base, preferably tertiary amine bases such as $(iPr)_2NEt$, pyridine, $NEt_3$ or DBU. Solvents which may be mentioned are any suitable aprotic solvents, for example DMF, THF, $CH_2Cl_2$ or mixtures thereof. The reaction is carried out at a temperature in the range from −20 to +40° C., preferably from −10 to +10°.

Reaction (b) is carried out at a temperature in the range from +10 to +130° C., preferably +20 to +70° C., in the presence of salts of amines and carboxylic acids, such as EDDA (ethylenediamine diacetate) or piperidinium acetate. It may be advantageous to add dehydrating agents such as $Na_2SO_4$ or orthoesters.

The subsequent cyclization (reaction (c)) takes place in the presence of a Lewis acid at a temperature in the range from +10 to +130° C., preferably from 0 to +40° C. However, the cyclization may also take place purely thermally in the absence of a catalyst. Preferred Lewis acids are $AlCl_3$, $AlBr_3$, $ZnBr_2$, $ZnCl_2$, $BF_3$, $BF_3 \times OEt_2$, $SnCl_4$, $Et_2AlCl$ or $TiCl_4$. Solvents which can be used for reactions (a) and (b) are any suitable aprotic solvents which are stable to Lewis acids.

If the compound III contains no olefinic double bond, and therefore the subsequent cyclization cannot be carried out, it is possible to react an external olefin with the product from reaction (b).

As carbon acid, compound II can in principle be used for all known C-C-linkage reactions of carbon acids (Organikum, Barth Verlagsgesellschaft mbH, 1993, 459–503), such as Michael addition, aldol condensation, Robinson annulation, palladium-catalyzed allylic substitutions or the Knoevenagel reaction. The Knoevenagel reaction is preferred.

Product I can be passed for mass screening directly or after elimination from the support.

The product I can be eliminated from the solid phase by reduction, transesterification, amidation or base catalysis (Scheme III). Reaction (d) is suitably carried out at a temperature in the range from −20 to +40° C., preferably −10 to +20° C., in the presence of a solvent and of a suitable reducing agent, for example DIBAH, $LiAlH_4$ or $LiBH_4$. The symmetrical diols are produced. Suitable solvents are any appropriate aprotic or protic solvents such as THF, ethers, MeOH or toluene.

Scheme III

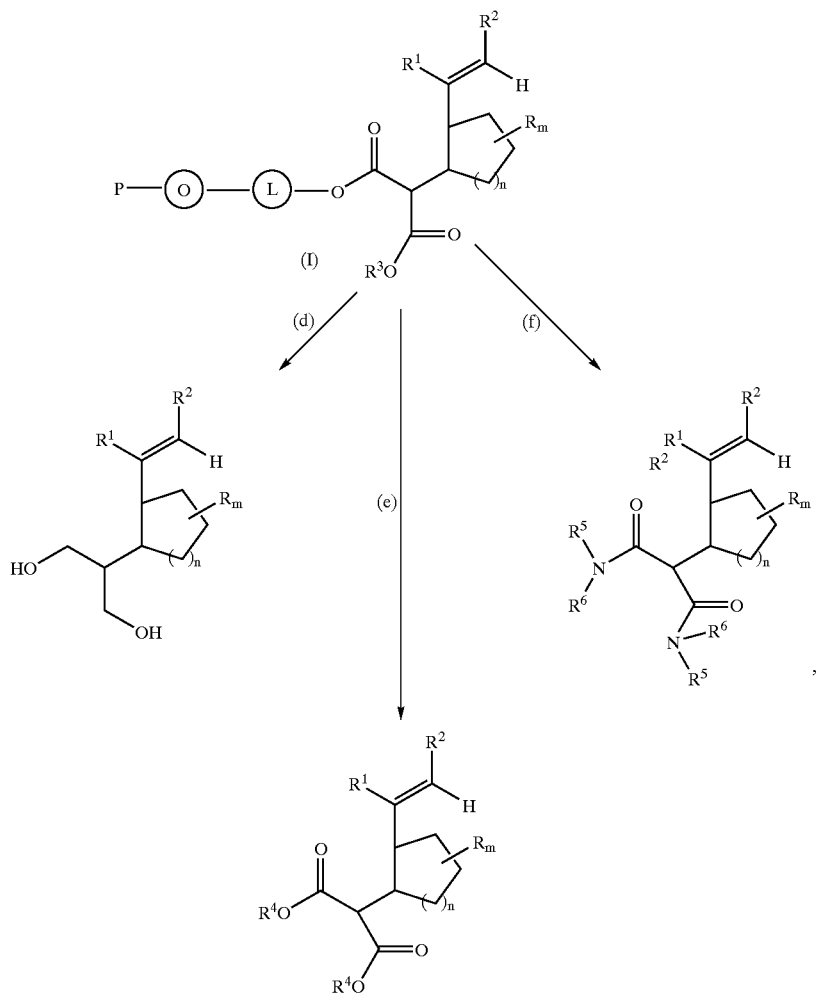

Reaction (e) for the transesterification is suitably carried out in a suitable solvent at a temperature in the range from +40 to +130° C., preferably +60 to +100° C., in the presence of $Ti(OR^7)_4$, where $R^7$ are branched or unbranched $C_1$–$C_6$-alkyl chains, preferably $Ti(OEt)_4$. Any appropriate ester is suitable as ester component. $R^4$ has the following meanings:
hydrogen
$C_1$–$C_{10}$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl, unsubstituted or substituted by an unsubstituted or substituted aromatic or heteroaromatic radical with 3 to 10 carbon atoms. The ring may contain one or more nitrogen, sulfur and/or oxygen atoms as hetero atoms.
$C_3$–$C_8$-Cycloalkyl such as cyclopropyl, cyclobutyl, cyclopentyl, cyclohexyl, cycloheptyl or cyclooctyl.

Aryl such as phenyl or naphthyl, each of which may be unsubstituted or substituted by halogen, such as fluorine, chlorine or bromine, cyano, nitro, amino, hydroxyl or thio.

Suitable solvents are any appropriate aprotic solvents such as $CH_2Cl_2$, toluene, THF or mixtures thereof.

If reaction (e) is to result in the free acid, compound I is preferably cleaved off the support with base catalysis. Suitable bases are any appropriate bases, for example NaOH, LiOH or KOH. The reaction is preferably carried out under reflux in the presence of a water-miscible solvent such as dimethoxyethane, THF, EtOH or MeOH. A suitable temperature is in the range from 60 to 130° C., preferably 95 to 110° C.

The aminolysis (reaction (f)) takes place in the presence of a suitable amine of the formula $NHR^5R^6$ at a temperature in the range from 60 to 130° C., preferably 70 to 90° C., in the presence or absence of an aprotic solvent such as toluene.

$R^5$ and $R^6$ have, independently of one another, the following meanings:
hydrogen
$C_1$–$C_{10}$-alkyl such as methyl, ethyl, n-propyl, n-butyl, 1-methylpropyl, 1-methylethyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl, unsubstituted or substituted by an unsubstituted or substituted aromatic or heteroaromatic radical with 3 to 10 carbon atoms. The ring may contain one or more nitrogen, sulfur and/or oxygen atoms as hetero atoms.

$C_3$–$C_8$-Cycloalkyl such as cyclopropyl, cyclobutyl, cyclopentyl, cyclohexyl, cycloheptyl or cyclooctyl.

Aryl such as phenyl or naphthyl, each of which may be unsubstituted or substituted by halogen such as fluorine, chlorine or bromine, cyano, nitro, amino, hydroxyl or thio.

The process according to the invention is very suitable for generating a large number of structurally diverse compounds of the formulae I, IV and VI, because the substituents R, $R^1$ to $R^7$ can be widely varied in a simple manner independently of one another.

Compared with reactions in solution, reactions on a polymeric support have great advantages. Thus, considerably fewer impurities are present in the products, so that chromatographic fractionation is unnecessary. In particular, the double-bond isomerization of the initially formed alkylidene-1,3-dicarbonyl compound which is frequently observed in solution scarcely occurs; in addition, the intramolecular carbonyl-ene reaction of the aldehydes, which occurs as side reaction, does not interfere because the corresponding alcohols are removed on washing the polymer-bound products. The good yields, the high purity of the eliminated products and the simple way of carrying out the reaction in the process according to the invention make it very attractive to use in the framework of combinatorial synthesis. A particular advantage of this process is, for example, the fact that it is unnecessary to use costly polymers because a low-cost linker can be attached to any solid phase for the functionalization.

The process is also particularly suitable for preparing defined mixtures of cycloalkyl derivatives of the formula I. This is done not by binding a single starting substance to the solid phase but by binding a mixture, preferably a mixture in which the stoichiometry and substances are known, to the solid phase.

The solid phase-bound reactant is then reacted by the described process with the other reactant and subsequently cyclized where appropriate.

It is thus possible, for example, to obtain 64 cycloalkyl derivatives starting from malonyl chloride monoesters, 8 aldehydes and subsequent elimination by transesterification with 4 different esters or aminolysis with 4 different amines by the method of Furka, A.; Sebestyen, F.; Asgedom, M.; Dibo, G. 1988, Abstr. 14th Int. Congr. Biochem, Prague, Czechoslovakia, Vol. 5, p 47. Abstr. 10th Int. Symp. Med. Chem., Budapest, Hungary, p. 288. Furka, A.; Sebestyen, F.; Asgedom, M.; Dibo, G. General Method for Rapid Synthesis of Multicomponent Peptide Mixtures. Int. J. Pept. Protein Res. 1991, 37, 487–493.

The advantage of this solid-phase synthesis is the rapid generation of a large number of single compounds which can subsequently be investigated for activity in test systems.

For this purpose, the substance mixtures can be either fractionated beforehand or employed directly in the form of the mixture. In the latter case, a potential active substance is identified after the testing.

The invention furthermore relates to the use of the process according to the invention for preparing bound or free cycloalkyl derivatives of the formulae I or IV to generate substance libraries.

By this is meant both the generation, described above, of cycloalkyl mixtures and the preparation of a large number of single substances of the formulae I, IV or VI, for example by carrying out many reactions of the same type, in which one reactant has been changed in each case, in parallel.

The carrying out of many reactions of the same type in parallel permits all the functional groups in the formulae I, IV or VI to be rapidly varied systematically.

The substance libraries which can be generated in this way can be rapidly tested for a particular activity in mass screening. This greatly speeds up the search for potent active substances.

The invention furthermore relates to cycloalkyl derivatives of the general formulae I, II or IV bound to a support. These compounds can be prepared by carrying out the abovementioned preparation process without eliminating the resulting cycloalkyl of the formula I or the intermediates II or IV from the solid phase.

This results in the cycloalkyls or the intermediates remaining bound to the solid phase, and they can easily be employed as such in test methods, preferably in in vitro test systems.

The advantage of the cycloalkyl derivatives and intermediates bound to the support is that they are easy to manipulate. For example, they can easily be isolated from the reaction solution by filtration or centrifugation.

In addition, the identification of an active substance is considerably facilitated because the cycloalkyl derivatives bound to a support are already in isolated form, and thus separation is unnecessary.

The following examples serve to illustrate the invention further without restricting it in any way.

EXAMPLE 1

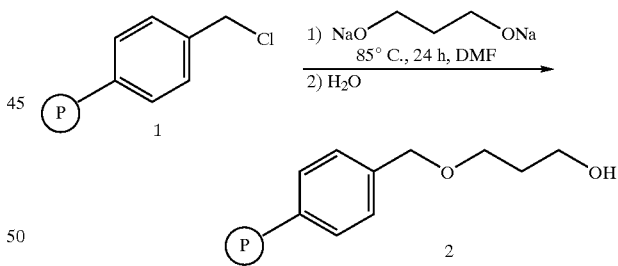

5 g of Merrifield resin 1 (2.58 mmol Cl/g, 2% DVB, Acros), swollen in DMF, were mixed with 26 ml of a 1M solution of disodium 1,3-propanediolate in DMF (26 mmol, 2 equivalents). The suspension was heated at 85° C. for 24 h. After cooling to about 60° C., 50 ml of water and the same volume of DMF were added. After stirring for a further 20 min, the linker-modified resin 2 was filtered off on a suction funnel, washed with DMF/water, DMF, methanol and methylene chloride and dried under water pump vacuum at 55° C. for 24 h.

The reaction was carried out similarly with 1,5-pentanediol.

To determine the concentration of hydroxyl groups in the resin 2 with attached linker, the latter was reacted with 3,5-dinitrobenzoyl chloride in pyridine, and determination of nitrogen in the resulting ester revealed 0.75 mmol of hydroxyl groups per gram of resin.

EXAMPLE 2

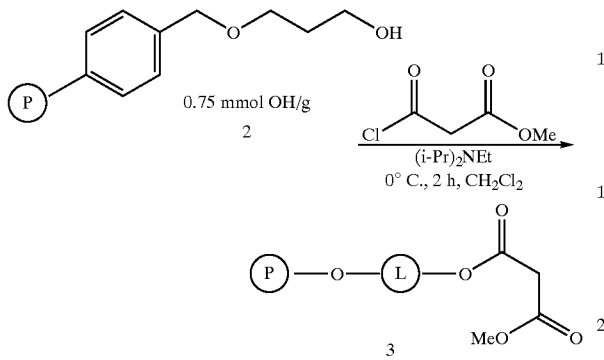

In a glass apparatus under a protective gas atmosphere, a suspension of the resin 2 (2.5 g) swollen in methylene chloride (12 ml) is mixed with 642 μl of Hünig base (diisopropylethylamine; 3.75 mmol, 2 equivalents) and cooled to 0° C. While vigorously stirring, 402 μl of methyl malonyl chloride (3.75 mmol, 2 equivalents) are slowly added dropwise. After the addition is complete, the mixture is stirred at the same temperature for 2 h and subsequently at 20° C. for 1 h. The resin 3 is filtered off, washed with methanol and methylene chloride and dried under water pump vacuum at 55° C.

The reaction was carried out similarly with the following resin:

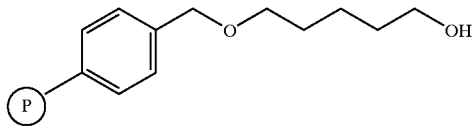

EXAMPLE 3

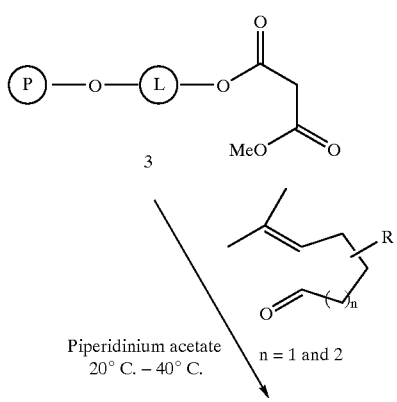

-continued

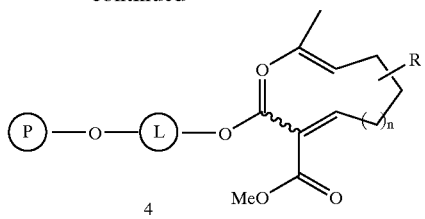

In a glass apparatus under a protective gas atmosphere, the malonate-functionalized polymer 3 (1 g) swollen in methylene chloride (6 ml) is mixed with the appropriate aldehydes (3 equivalents). The mixture is stirred at 20° C. for 30 min. After successive addition of 8.6 μl of 99.9% pure acetic acid (0.15 mmol, 0.2 equivalent based on polymeric malonate) and 14.8 μl of freshly distilled piperidine (0.15 mmol, 0.2 equivalent based on polymeric malonate). The reaction is allowed to continue for 2 h and then the same amount of catalyst is added once again and stirring is continued for one hour. After the reaction is complete, the resin 4 is filtered off and washed with methylene chloride and not sucked dry (exclusion of moisture).

When α-substituted aldehydes are used, freshly heated sodium sulfate (about 5 spatula tips on use of 1 g of resin) is also added. The temperature is preferably raised to 40° C. The reaction mixture is refluxed, the procedure being otherwise the same.

The reactions (i.e. the reaction of the aldehydes) can be followed by GC with 1-dodecene as internal standard.

EXAMPLE 4

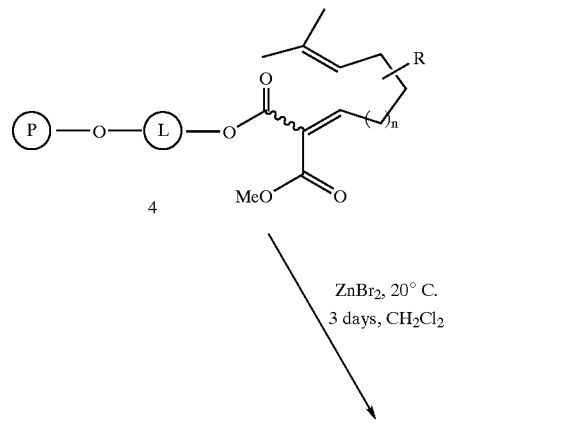

In a glass apparatus under a protective atmosphere, the resin 4 (about 1 g, see above) swollen in methylene chloride (7 ml) is mixed with 202 mg of freshly heated zinc bromide (0.83 mmol, 1.1 equivalent). The suspension is stirred at 20° C. for 3 days. Subsequently, the suspended zinc bromide is dissolved with methanol. The resin 5 is filtered off, washed with methanol and methylene chloride and dried under water pump vacuum at 55° C. for 24 h.

EXAMPLE 5

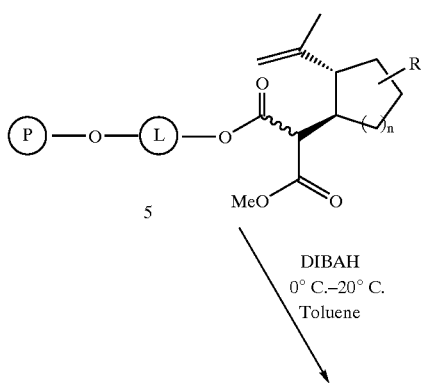

In a glass apparatus under a protective gas atmosphere, the resin 5 (1 g) swollen in toluene (5 ml) is cooled to 0° C. and 10 ml of a 1.2 molar diisobutylaluminum hydride solution (DIBAH) in toluene (12 mmol, 4 equivalents/ester functionality) are added dropwise. After the addition is complete, the mixture is allowed to reach 20° C. overnight. To destroy excess DIBAH, methanol is cautiously added to the reaction mixture cooled in ice (the reaction mixture may become a gelatinous solid). The mixture is then vigorously shaken with the same volume (based on the complete reaction mixture) of a potassium sodium tartrate solution, and the organic phase is separated off. The resin collects mainly at the phase boundary and need not be removed in a separate step. The aqueous phase is extracted with tert-butyl methyl ether until diol is no longer detectable. The combined organic phases are washed with NaCl solution and dried over anhydrous $Na_2SO_4$ and then concentrated under reduced pressure, and the residue is dried under oil. pump vacuum.

EXAMPLE 6

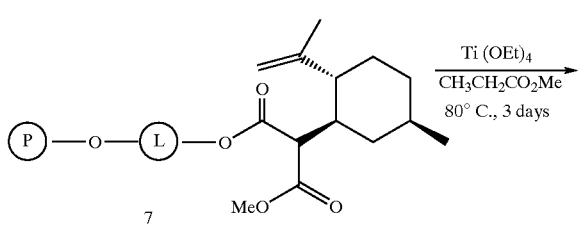

In a glass apparatus under a protective atmosphere, 1 g of resin 7 is suspended in 10 ml of dry methyl propionate. 157 μl of $Ti(OEt)_4$ (0.75 mmol, 1 equivalent) are added and the mixture is then refluxed for 3 days. After cooling to 20° C., about 20 ml of 2 N HCl are added to the reaction mixture, which is then vigorously shaken. The resin collects mainly at the phase boundary and need not be removed in a separate step. After separation of the phases, the aqueous phase is extracted several times with tert-butyl methyl ether. The collected organic phases are washed with $NaHCO_3$, dried over anhydrous $Na_2SO_4$ and evaporated to dryness under reduced pressure. 82 mg of compound 8 are obtained (41% of the theoretical yield, based on the concentration of free OH groups in the spacer-modified polymer).

EXAMPLE 7

The reaction sequence described as carried out separately in Examples 3 to 6 can also be carried out in one reaction vessel without isolating the individual intermediates,

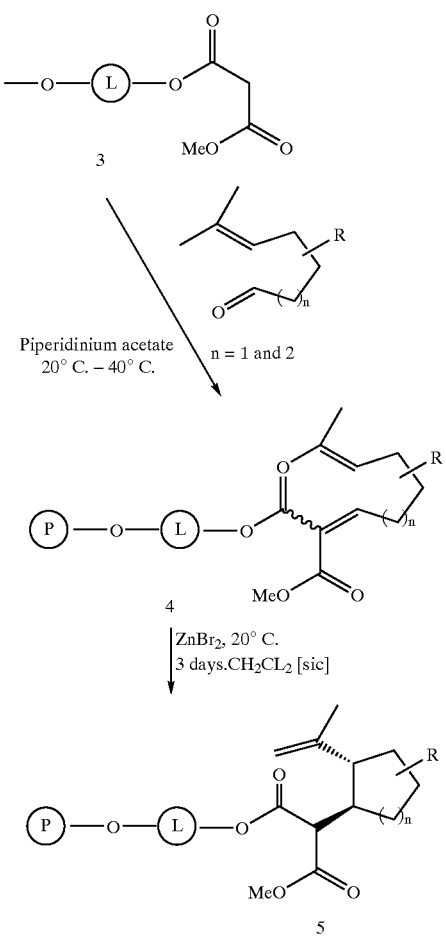

In a glass apparatus under a protective atmosphere, the malonate-functionalized polymer 3 (1 g) swollen in methylene chloride (6 ml) is mixed with the appropriate aldehydes (3 equivalents). The mixture is stirred at 20° C. for 30 min. After successive addition of 8.6 μl of 99.9% pure acetic acid (0.15 mmol, 0.2 equivalent based on polymeric malonate) and 14.8 μl of freshly distilled piperidine (0.15 mmol, 0.2 equivalent based on polymeric malonate), the reactions are allowed to continue for 2 h and then the same amount of catalyst is added once again and stirring is continued for one hour. 202 mg of freshly heated zinc bromide (0.83 mmol, 1.1 equivalent) and 1 ml of methylene chloride are added. The suspension is stirred at 20° C. for 3 days. The suspended zinc bromide is then dissolved with methanol. The resin 5 is filtered off, washed with methanol and methylene chloride and dried under water pump vacuum at 55° C. for 24 h.

TABLE 1

Yields and diastereoselectivities in Examples 3 to 7

| Substrate | Main product | Yield [%] [a] | Diastereoselectivity trans:cis [b] |
|---|---|---|---|
| (a) | | 61 | 98.5:1.5 |
| | | 63 | >99:1 |
| (c) | + diastereomer 97.2:2.8 | 61 | >99:1 |
| (b) | | 59 | >99:1 |
| | + diastereomer 78:22 [c] | 51 | >99:1 |

TABLE 1-continued

Yields and diastereoselectivities in Examples 3 to 7

| Substrate | Main product | Yield [%] [a] | Diastereo-selectivity trans:cis [b] |
|---|---|---|---|
| (structure) | (structure) + diastereomer 58:42 | 48 | >99:1 |

[a] The total yield is based on the concentration of free hydroxyl groups in the polymer
[b] GC analysis of the silylated crude products
[c] The assignment of the main product took place on the assumption of a transitional structure in chair form, taking account of the preferred orientation of the geminal substituents The products can be prepared in good yields and in high purity, and excellent simple and induced diastereoelectricity, both in this one-pot variant and in Examples 3 to 6. The yields, based on free hydroxyl groups in the polymer, were 41 to 61%. The purity of the products after elimination was normally 90%. The cyclization reaction (Ene reaction) is unaffected with regard to the simple and induced diastereoselectivity by the binding to the polymer (see Table 1). Trans-1,2-disubstituted cyclohexanes were obtained with a simple diastereoselectivity ds of >99:1 and the corresponding trans-1,2-disubstituted cyclopentanes were obtained with ds=98.5:1.5.

The induced diastereoselectivity in the case of the α-mono-substituted aldehydes a and b was in each case ds>99:1, whereas an induced diastereoselectivity of ds=96.9:3.1 was found with the β-monosubstituted aldehyde c.

Spectroscopic data for 3 examples

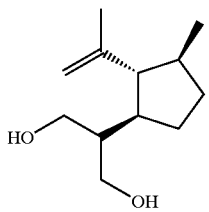

$^1$H-NMR (CDCl$_3$, 200 MHz): δ=0.89 (d, J=6 Hz; 3H, 3'-CH$_3$), 0.96–1.89 (m; 7H, other protons), 1.68 (mc; 3H, 2"-CH$_3$), 1.98 (mc; 1H), 2.38 (s br; 2H, OH, exchangeable with D$_2$O), 3.53–3.93 (m; 4H, 1-H$_2$, 3-H$_2$), 4.82 (mc; 2H, 1"-H$_2$). $^{13}$C-NMR (CDCl$_3$, 20 MHz): δ=18.21 and 18.91 (C-3" and 3'-CH$_3$), 27.51 (C-5'), 32.83 (C-4'), 38.68 (C-3'), 41.43 (C-1'), 45.64 (C-2), 60.42 (C-2'), 63.53 and 64.58 (C-1 and C-3), 112,44 (C-1"), 146.75 (C-2"). MS (70 eV): m/e= 198 (1%, M$^+$), 183 (2% M-CH$_3$), 180 (9%, M-H$_2$O), 165 (10%, 180-CH$_3$), 123 (100%, C$_9$H$_{15}$), 109 (41%), 107 (42%, C$_8$H$_{11}$), 93 (36%, C$_7$H$_9$), 83 (45%, C$_6$H$_{11}$), 82 (35%) 81 (80%, C$_6$H$_9$), 79 (37%, C$_6$H$_7$), 67 (54%, C$_5$H$_7$), 55 (58%, C$_4$H$_7$), 43 (34%, C$_3$H$_7$), 41 (65%, C$_3$H$_5$).

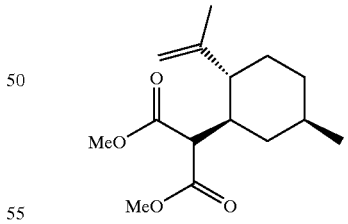

$^1$H-NMR (CDCl$_3$, 200 MHz): δ=0.64 (q, J=12 Hz; 1H, 6'-H$_{ax}$), 0.87 (d, J=6.5 Hz; 3H, 5'-CH$_3$), 0.91 (d q, J=4, 12 Hz; 1H, 3'-H$_{ax}$ or 4'-H$_{ax}$), 1.14–1.82 (m; 6H, other protons), 1.66 (mc; 3H, 2"-CH$_3$), 1.84–2.06 (m; 2H), 2.17 (mc; 1H, OH, exchangeable with D$_2$O), 2.37 (mc; 1H, OH, exchangeable with D$_2$O), 3.56–3.76 (m; 2H, 1-H$_2$ or 3-H$_2$, signal sharper after D$_2$O exchange), 3.78–4.00 (m; 2H, 1-H$_2$ or 3-H$_2$, signal sharper after D$_2$O exchange), 4.78 (s br; 2H, 1"-H$_2$). $^{13}$C-NMR (CDCl$_3$, 50 MHz): δ=18.43 (C-3"), 22.72 (5'-CH$_3$), 32.65 (C-3'), 32.97 (C-5'), 34.93 (C-4'), 35.96 (C-6'), 39.60 (C-1'), 42.96 (C-2), 49.14 (C-2'), 62.96 and 66.73 (C-3), 111.76 (C-1"), 148.50 (C-2"). MS (70 eV): m/e=212 (0.3%, M$^+$, HA), 194 (8%, M-H$_2$O), 151 (17%, M-C$_2$H$_5$O$_2$), 137 (67%, C$_{10}$H$_{17}$), 109 (43%), 107 (41%), 95 (79%, C$_7$H$_{11}$), 93 (49%), 81 (100%, C$_6$H$_9$), 69 (51%, C$_5$H$_9$), 67 (51%, C$_5$H$_7$), 55 (51%, C$_4$H$_7$), 41 (60%, C$_3$H$_5$).

(structure)

$^1$H-NMR (CDCl$_3$, 200 MHz): δ=0.91 (d, J=6,5 Hz; 3H, 5'-CH$_3$), 0.95 (d q, J=3.5, 12 Hz; 1H, 4'-H$_{ax}$), 1.11 (q, J=11.5 Hz; 1H, 6'-H$_{ax}$), 1.24–1.57 (m; 2H, 3'-H$_{ax}$, 5'-H$_{ax}$), 1.65 (mc; 3H, 2"-CH$_3$), 1.57–1.94 (m; 3H, 3'-H$_{eq}$, 4'-H$_{eq}$, 6'H$_{eq}$), 2.05 (d t, J=3.0, 11.5 Hz; 1H, 2'H), 2.13 (t t, J=3.5, 11.5 Hz; 1H, 1'H), 3.56 (d, J=3.5 Hz; 1H, 2-H), 3.73 (s; 6H, OCH$_3$), 4.74 (mc; 1H, 1"-H), 4.79 (m; 1H, 1"H). $^{13}$C-NMR (CDCl$_3$, 50 MHz): δ=18.96 (C-3"), 22,54 (5'-CH$_3$), 32.35 (C-3'), 32.73 (C-5'), 34.68 (C-4'), 36.59 (C-6'), 39.88 (C-1'), 48.68 (C-2'), 51.80 and 52.22 (OCH$_3$), 53.22 (C-2), 112.43 (C-1"), 147.52 (C-2"), 169.03 and 170.11 (C-1 and C-3). MS (70 eV):

m/e=268 (4%, M+), 250 (1%, M—H$_2$O), 237 (3%, M—CH$_3$O), 236 (3%, M—CH$_3$OH), 209 (3%, M—C$_2$H$_3$O$_2$), 208 (7%, M—C$_2$H$_4$O$_2$), 137 (19%, C$_{10}$H$_{17}$), 136 (100%, C$_{10}$H$_{16}$, McL, HA), 133 (29%), 132 (16%, C$_5$H$_8$O$_4$), 121 (35%, C$_9$H$_{13}$), 107 (41%, C$_8$H$_{11}$), 94 (14%, C$_7$H$_{10}$, RDA), 93 (34%, C$_7$H$_9$), 79 (21%, C$_6$J$_7$), 59 (10%, C$_2$H$_3$O$_2$).

We claim:

1. A cycloalkyl compound of formula I

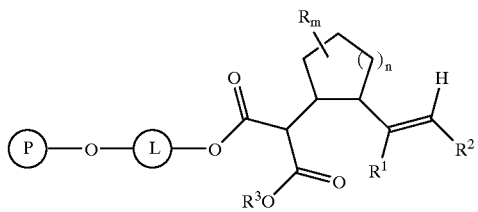
(I)

wherein

- Ⓟ is a solid phase,
- Ⓛ is a linking moiety with 2 to 12 carbon atoms, or is CH$_2$CH$_2$—(O—CH$_2$CH$_2$)$_{1-100}$,
- $R^1$ is hydrogen, or is alkyl, alkenyl, alkynyl, cycloalkyl, cycloalkenyl, cycloalkynyl, aryl, hetaryl, alkylaryl, alkylhetaryl, alkylcarbonyl, arylcarbonyl, alkylsulfonyl or arylsulfonyl of from 1 to 26 carbon atoms;
- $R^2$ is hydrogen or unsubstituted or substituted alkyl, alkenyl, alkynyl or cycloalkyl, or
- $R^1$ and $R^2$ are linked to form an unsubstituted or substituted 4- to 8-membered ring,
- $R^3$ is unsubstituted or substituted C$_1$–C$_{10}$-alkyl, C$_3$–C$_8$-cycloalkyl or aryl,
- R is alkyl, alkenyl, alkynyl, cycloalkyl, aryl, hetaryl, alkylaryl, alkylhetaryl, alkylcarbonyl, arylcarbonyl, alkylsulfonyl or arylsulfonyl of from 1 to 26 carbon atoms, or two adjacent R radicals are linked to form an unsubstituted or substituted carbo- or heterocyclic ring,
- n is 0 to 4, and
- m is 0 to n+2, which is obtained by preparing a compound of formula II

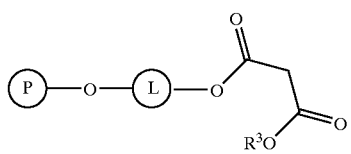
(II)

by linking a compound of formula VII

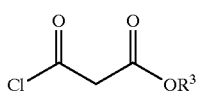
(VII)

to a functionalized solid phase of formula V

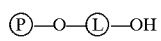
(V)

in the presence of a base, reacting the compound of formula II with an aldehyde of formula III

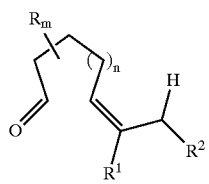
(III)

in the presence of a base to give a compound of formula IV

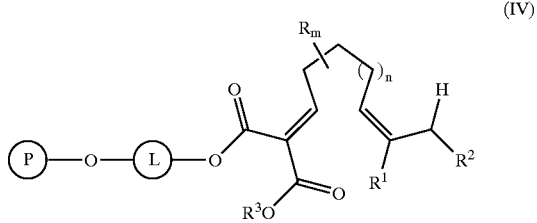
(IV)

and cyclizing the compound of formula IV in the presence of a Lewis acid.

2. The cycloalkyl compound of formula I defined in claim 1, wherein
- $R^2$ is hydrogen, or is C$_1$–C$_8$-alkyl, C$_2$–C$_8$-alkenyl, C$_2$–C$_6$-alkynyl or C$_3$–C$_8$-cycloalkyl;
- $R^3$ is C$_1$–C$_{10}$-alkyl, C$_3$–C$_8$-cycloalkyl, phenyl or naphthyl;
- R is alkyl, alkenyl, alkynyl, cycloalkyl, aryl, hetaryl, alkylaryl, alkylhetaryl, alkylcarbonyl, arylcarbonyl, alkylsulfonyl or arylsulfonyl of from 1 to 26 carbon atoms, or two adjacent R radicals are linked to form a carbocyclic ring.

3. The cycloalkyl compound of formula I defined in claim 1, wherein
- $R^1$ is hydrogen, or is C$_1$–C$_8$-alkyl, C$_2$–C$_8$-alkenyl, C$_2$–C$_6$-alkynyl, C$_3$–C$_8$-cycloalkyl, phenyl or naphthyl;
- $R^2$ is hydrogen, or is C$_1$–C$_8$-alkyl, C$_2$–C$_8$-alkenyl, C$_2$–C$_6$-alkynyl or C$_3$–C$_8$-cycloalkyl;
- $R^3$ is C$_1$–C$_{10}$-alkyl, C$_3$–C$_8$-cycloalkyl, phenyl or naphthyl;
- R is C$_1$–C$_8$-alkyl, C$_2$–C$_8$-alkenyl, C$_2$–C$_6$-alkynyl, C$_3$–C$_8$-cycloalkyl, phenyl or naphthyl.

4. The cycloalkyl compound of formula I defined in claim 1, wherein n is 1 or 2.

5. The cycloalkyl compound of formula I defined in claim 1, wherein R, $R^1$ and $R^3$ are methyl, $R^2$ is hydrogen and n and m are each 1.

6. A process for preparing a cycloalkyl compound of formula I

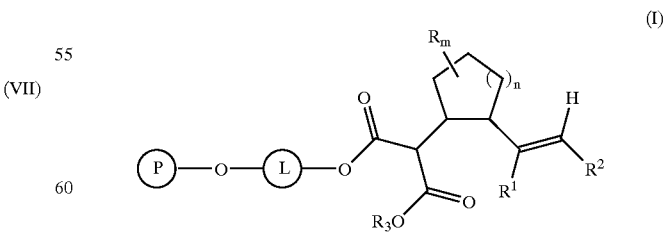
(I)

wherein
- Ⓟ is a solid phase,
- Ⓛ is a linking moiety with 2 to 12 carbon atoms, or is CH$_2$CH$_2$—(O—CH$_2$CH$_2$)$_{1-100}$, $R^1$ is hydrogen, or is alkyl, alkenyl, alkynyl, cycloalkyl, cycloalkenyl, cycloalkynyl, aryl, hetaryl, alkylaryl, alkylhetaryl, alkylcarbonyl, arylcarbonyl, alkylsulfonyl or arylsulfonyl of from 1 to 26 carbon atoms;

$R^2$ is hydrogen or unsubstituted or substituted alkyl, alkenyl, alkynyl or cycloalkyl, or $R^1$ and $R^2$ are linked to form an unsubstituted or substituted 4- to 8-membered ring, $R^3$ is unsubstituted or substituted $C_1$–$C_{10}$-alkyl, $C_3$–$C_8$-cycloalkyl or aryl, R is alkyl, alkenyl, alkynyl, cycloalkyl, aryl, hetaryl, alkylaryl, alkylhetaryl, alkylcarbonyl, arylcarbonyl, alkylsulfonyl or arylsulfonyl of from 1 to 26 carbon atoms, or two adjacent R radicals are linked to form an unsubstituted or substituted carbo- or heterocyclic ring, n is 0 to 4, and m is 0 to n+2, which comprises preparing a compound of formula II

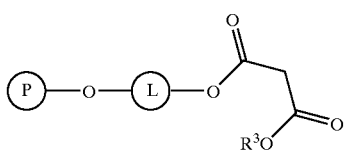

(II)

by linking a compound of formula VII

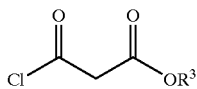

(VII)

to a functionalized solid phase of formula V

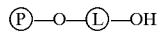

(V)

in the presence of a base, reacting the compound of formula II with an aldehyde of formula III

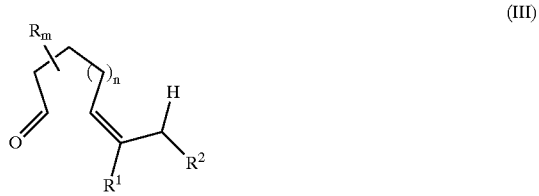

(III)

in the presence of a base to give a compound of formula IV

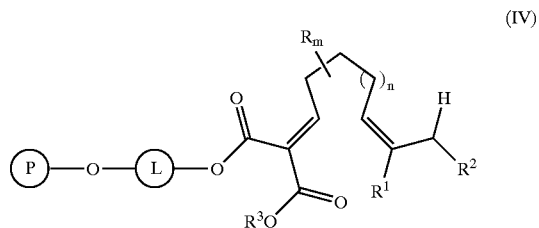

(IV)

and cyclizing the compound of formula IV in the presence of a Lewis acid.

7. The process of claim 6, wherein the solid phase ⓟ is selected from the group consisting of ceramic, glass, latex, cross-linked polystyrenes, polyacrylamides, silica gels, cellulose particles, resins, gold and colloid metal particles.

8. The process of claim 7, wherein the solid phase ⓟ is selected from the group consisting of latex, crosslinked polystyrenes, polyacrylamides, cellulose particles and resins.

9. The process of claim 8, wherein the solid phase is selected from the group consisting of a polyacrylamide, a chlorobenzyl-resin, a Rink resin, a Sieber resin, a Wang resin, a Tentagel resin and a Pega resin.

10. The process of claim 6, wherein the moiety O—ⓛ—O corresponds to a diol of formula HO—ⓛ—OH selected from the group consisting of ethylene glycol, 1,3-propanediol, 1,2-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,4-pentanediol, 2-methyl-1,4-butanediol, 1,2-hexanediol, 1,3-hexanediol, 1,4-hexanediol, 1,5-hexanediol, 1,6-hexanediol, two adjacent R radicals are linked to form a carbocyclic ring.

* * * * *

UNITED STATES PATENT AND TRADEMARK OFFICE
CERTIFICATE OF CORRECTION

PATENT NO.   : 6,521,780 B1
DATED        : February 18, 2003
INVENTOR(S)  : Tietze et al.

It is certified that error appears in the above-identified patent and that said Letters Patent is hereby corrected as shown below:

<u>Column 28,</u>
Line 27, "cross-linked" should be -- crosslinked --.
Line 43, "two adjacent R radicals are linked to form a carbocyclic ring" should be -- 2,3-hexanediol, 2,4-hexanediol, 2-methyl-1,5-pentanediol and 3-methyl-1,5-pentanediol --.

Signed and Sealed this

Seventeenth Day of June, 2003

JAMES E. ROGAN
*Director of the United States Patent and Trademark Office*